United States Patent [19]

Müller et al.

[11] Patent Number: 4,906,752

[45] Date of Patent: Mar. 6, 1990

[54] **LIQUID-CRYSTAL 5-PHENYLPYRIMIDINE DERIVATIVES HAVING SC OR SC* PHASES AND A PROCESS FOR PREPARING THEM**

[75] Inventors: Ingrid Müller, Hofheim am Taunus; Hans-Rolf Dübal, Königstein/Taunus; Claus Escher, Mühltal; Wolfgang Hemmerling, Sulzbach; Dieter Ohlendorf, Liederbach; Rainer Wingen, Hattersheim am Main, all of Fed. Rep. of Germany

[73] Assignee: Hoechst Aktiengesellschaft, Frankfurt am Main, Fed. Rep. of Germany

[21] Appl. No.: 378,466

[22] Filed: Jul. 12, 1989

Related U.S. Application Data

[63] Continuation of Ser. No. 172,701, Mar. 22, 1988, abandoned.

[30] Foreign Application Priority Data

Mar. 24, 1987 [DE] Fed. Rep. of Germany ....... 3709618

[51] Int. Cl.$^4$ .......................... G02F 1/13; C09K 19/34; C07D 239/02
[52] U.S. Cl. ............................... 544/318; 252/299.01; 252/299.61; 350/350 R; 350/350 S; 544/242; 544/315; 544/335
[58] Field of Search .................. 252/299.01, 299.61; 350/350 S, 350 R; 544/242, 315, 318, 335

[56] References Cited

U.S. PATENT DOCUMENTS

| | | | |
|---|---|---|---|
| 4,565,425 | 1/1986 | Petrzilka et al. | 252/299.61 |
| 4,676,604 | 6/1987 | Petrzilka | 252/299.61 |
| 4,776,973 | 10/1988 | Bofinger et al. | 252/299.61 |
| 4,780,241 | 10/1988 | Furukawa et al. | 252/299.61 |
| 4,818,428 | 4/1989 | Scheuble et al. | |
| 4,820,839 | 4/1987 | Krause et al. | 252/299.61 |
| 4,834,904 | 5/1989 | Krause et al. | 252/299.61 |

FOREIGN PATENT DOCUMENTS

| | | | |
|---|---|---|---|
| 199004 | 10/1986 | European Pat. Off. | 252/299.61 |
| 0199004 | 10/1986 | European Pat. Off. | |
| 206228 | 12/1986 | European Pat. Off. | 252/299.61 |
| 225195 | 6/1987 | European Pat. Off. | 252/299.61 |
| 260077 | 3/1988 | European Pat. Off. | 252/299.61 |
| 269062 | 6/1988 | European Pat. Off. | 252/299.61 |
| 3500897 | 7/1986 | Fed. Rep. of Germany | 252/299.61 |
| 3506446 | 8/1986 | Fed. Rep. of Germany | 252/299.61 |
| 3515373 | 11/1986 | Fed. Rep. of Germany | 252/299.61 |
| 3515374 | 11/1986 | Fed. Rep. of Germany | 252/299.61 |
| 3518734 | 11/1986 | Fed. Rep. of Germany | 252/299.61 |
| 145913 | 1/1981 | German Democratic Rep. | 252/299.61 |
| 6348270 | 2/1988 | Japan | 252/299.61 |
| 8606401 | 11/1986 | World Int. Prop. O. | 252/299.61 |
| 8705018 | 8/1987 | World Int. Prop. O. | 252/299.61 |

OTHER PUBLICATIONS

C. A. 87: 184456d (1977).
C. A. 110:67361b (1989).
Shama, N. K. et al., Molecular Crystals Liq. Cryst., vol. 151, pp. 225–231 (1987).
Demus D. et al., Flussice Kristalle in Tabellen II, Ved Deutscher Verlag fur Grundstoffindustrie, Leipzig, pp. 378–388 (1984).
Zaschke H., Advances in Liquid Crystal Research and Application, Bata, L., Ed., Pergamen Press, Oxfors, pp. 1059–1074 (1980).
Zaschke et al., Chemical Abstracts, vol. 87, p. 608, 184456d (1977).
Mueller et al., Chemical abstracts, vol. 110, p. 659, 67361b (1989).

Primary Examiner—Teddy S. Gron
Attorney, Agent, or Firm—Curtis, Morris & Safford

[57] ABSTRACT

Liquid-crystal 5-phenylpyrmidine derivatives having $S_c$ or $S^*_c$ phases and a process for preparing them. The new liquid-crystal 5-phenylpyrimidine derivatives have an $S_c$ or $S^*_c$ phase and are described by the general formula (I)

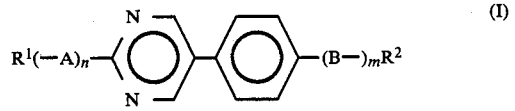

in which the symbols have the following meaning:
$R^1$ and $R^2$ denote identical or different, straight-chain or branched alkyl or alkenyl groups having from k to 16 carbon atoms, with or without an asymmetric carbon atom, in which one or more non-adjacent —CH$_2$— groups can be replaced by —O— and /or —S——A and —B each denote

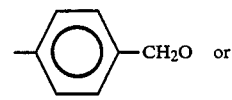

or

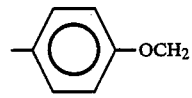

in which the radicals $R^1$, $R^2$, in each case, are situated at the phenylene part of —A, —B and
m and n denote 0 or 1, but m and n do not simultaneously denote 1, with the following provisos:
(a) if m=n=0, k is 8, and in $R^2$ the —CH$_2$— group adjacent to the phenyl nucleus is replaced by —O—;
(b) if m=1 and n=0, k is 2, and
(c) if m=0 and n=1, k is 2 and in $R^2$ the —CH$_2$— group adjacent to the phenyl nucleus is replaced by —O—.

2 Claims, No Drawings

LIQUID-CRYSTAL 5-PHENYLPYRIMIDINE DERIVATIVES HAVING SC OR SC* PHASES AND A PROCESS FOR PREPARING THEM

This application is a continuation of application Ser. No. 172,701, filed Mar. 22, 1988, now abandoned.

Liquid crystals have recently been introduced into a wide range of technical fields in which electrooptical and display device properties are in demand (for example in watch, pocket-calculator and typewriter displays). These display devices are based on the effects of dielectric alignment in the nuematic, cholesteric and/or smectic phases of liquid-crystal compounds, the molecular longitudinal axis of the compounds, due to the dielectric anisotropy, adopting a certain alignment in an applied electrical field. The usual switching times in these display devices are rather too slow for many other potential areas of application of liquid crystals, which are per se highly promising chemical compounds for industry due to their unique properties. This disadvantage is particularly noticeable if—which is necessarily the case in large display element areas—it is necessary to address a large number of image points, which means that the production costs of such instruments containing these larger areas, such as video equipment, oscillographs or TV, radar, EDP or word processor screens, would be too high.

Besides the nematic and cholesteric liquid crystals, ferroelectric, smectic liquid-crystal phases have in the last few years become increasingly important even for practical applications.

Clark and Lagerwall have been able to show that the use of such liquid-crystal systems in very thin cells leads to optoelectric switching or display elements which, compared to conventional TN ("twisted nematic") cells have switching times which are faster by a factor of about 1,000 (cf. for example Lagerwall et al. "Ferroelectric Liquid Crystals for Displays", SID Symposium, October Meeting 1985, San Diego, Calif., USA). As a consequence of these and other favorable properties, for example the possibility for bistable switching and the contrast which is virtually independent of the view angle, FLCs are generally highly suitable for the above-mentioned areas of application, for example via matrix addressing.

For practical use of ferroelectric liquid crystals in optoelectric displays, chirally tilted, smectic phases, for example $S_c^*$ phases, are required (R. B. Meyer, L. Liébert, L. Strzelecki, P. Keller, J. Physique 36, L-69 (1975)), which are stable over a large temperature range.

This goal can be achieved using compounds which themselves form chiral smectic phases, for example $S_c^*$ phases or, on the other hand, by doping non-chiral compounds which form tilted smectic phases with optically active compounds (M. Brunet, C. Williams, Ann. Phys. 3, 237 (1978)).

Therefore, there is a demand for compounds which form smectic phases and by means of which mixtures forming smectic, in particular $S_c$ or $S_c^*$ phases, can be prepared.

Surprisingly, it has now been found that the novel compounds of the formula (I) form liquid-crystal $S_c$ and/or $S_c^*$ phases.

The 5-phenylpyrimidine derivatives are those in which the symbols in the formula (I)

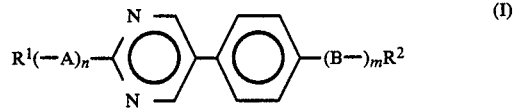

have the following meaning:

$R^1$ and $R^2$ denote identical or different, straight-chain or branched alkyl or alkenyl groups having from k to 16 carbon atoms, with or without an asymmetric carbon atom, in which one or more non-adjacent —CH$_2$—groups can be replaced by —O— and/or —S—, —A and —B each denote

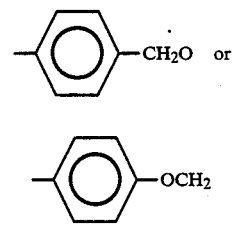

in which the radicals $R_1$, $R_2$, in each case, are situated at the phenylene part of —A, —B and m and n denote 0 or 1, but m and n do not simultaneously denote 1, with the following provisos:
(a) if m=n=0, k is 8, and in $R^2$ the —CH$_2$— group adjacent to the phenyl nucleus is replaced by —O—;
(b) if m=1 and n=0, k is 2, and
(c) if m=0 and n=1, k is 2 and in $R^2$ the —CH$_2$— group adjacent to the phenyl nucleus is replaced by —O—.

Compounds of the formula (I) having $R^1$ =n-hexyl, $R^2$ =(C$_1$- to C$_{10}$-n-alkyl)oxy and m=n=0 are known (H. Zaschke, Diss. B, Univ. Halle/S. 1977). However, those compounds only have $S_A$, $S_B$ and monotropic $S_G$ phases.

Compounds of the formula (I) having $R^1$=(C$_1$- to C$_{10}$-n-alkyl)thio, $R^2$=(C$_1$- to C$_{10}$-n-alkyl)oxy and m=n=0 are also known (H. Zaschke et al., Z. Chem. 17, 293 (1977)). They have been shown to have only an $S_A$ phase.

Compounds of the formula (I) having $R^1$=n-hexyloxy, $R^2$=(C$_4$- to C$_6$-n-alkyl)oxy and m=n=0 are also known (H. Zaschke, Diss. B, Univ. Halle/S., 1977). Again, for these compounds, too, only $S_A$ phases have been found.

In contrast to common knowledge - as it is for example documented in "Flüssigkristalle in Tabellen" (Liquid Crystals in Tables), D. Demus, (editor) VEB Deutscher Verlag fur Grundstoffindustrie, Leipzig, vol. I (1974), vol. II (1984)—it has now been found, suprisingly, that the novel compounds of the formula (I) possess liquid-crystal $S_c$ and/or $S_c^*$ phases.

This finding is particularly surprising because, based on the extensive and systematic variations of the substituents $R^1$ and $R^2$ as described in the articles cited above, the appearance of $S_c$ or $S_c^*$ phases was not to be expected. Some of the novel compounds even possess a very wide and predominantly favorable $S_c$ and/or $S_c^*$ range in terms of temperature, that is at relatively low temperatures.

The preparation of the known compound (I) having $R^1$=n-hexyl, $R^2$=(C$_1$- to C$_{10}$-alkyl)oxy and m=n=0 has been described in the abovementioned literature as follows:

an amidinium salt (II) is condensed with a 1-dimethylamino-3-dimethyliminio-2-(4-$R^2$-phenyl)-1-propene perchlorate (III) to give (I).

For compounds of the formula (I) having $R^1$=($C_1$- to $C_{10}$-n-alkyl)thio, $R^2$=($C_1$ to $C_{10}$-n-alkyl)oxy and m=n=0, a preparative method has been described in which an S-alkyl isothiourea bromide (IV) is reacted with a 1-dimethylamino-3-dimethyliminio-2-(4-$R^2$-phenyl)-1-propene perchlorate (III) in pyridine.

For compounds of the formula (I) having $R^1$=n-hexyloxy, $R^2$=($C_4$- to $C_6$-n-alkyl)oxy and m=n=0, the following procedure is given: the 1-dimethylamino-3-dimethyliminio-2-(4-$R^2$-phenyl)-1-propene perchlorate (III) is reacted with urea to give 2-pyrimidinone (V). Chlorination of (V) to give the 2-chloropyrimidine compound (VI) using phosphorus oxychloride and finally $S_N$ reaction of (VI) with sodium hexanolate to give (I) are the next steps.

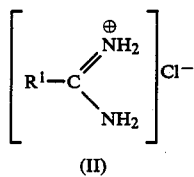

(II)

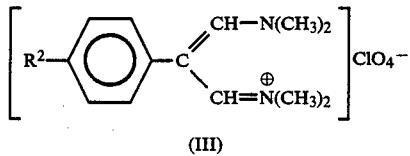

(III)

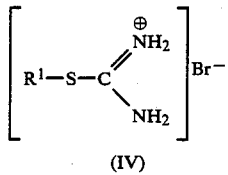

(IV)

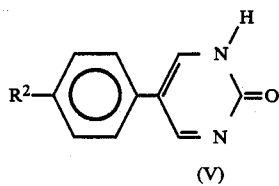

(V)

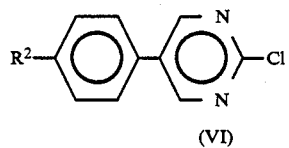

(VI)

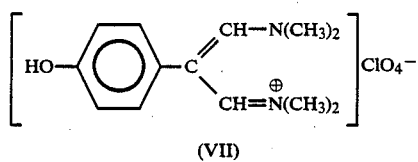

(VII)

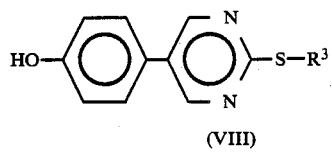

(VIII)

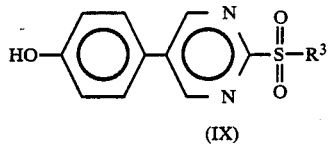

(IX)

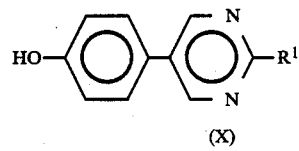

(X)

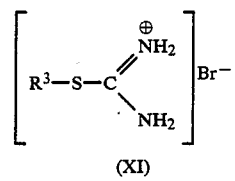

(XI)

By virtue of the starting materials used in these processes, the substituents $R^1$ and $R^2$ are already determined in the first step of the synthesis in either case. This is especially true for (III) in which $R^2$ is determined. A wide variation of substituents is therefore only possible using the corresponding number of homologous starting materials.

By using the process which is subsequently described in more detail and is also an embodiment of the invention, this disadvantage is removed: by using (VII) for the ring closure reactions, wide variation in $R^2$ is possible, since the free hydroxyl group can be reacted in subsequent reactions with any desired compounds which contain the $R^2$ partial structure in a suitable form. The synthesis is particularly economical, since it uses a central starting material (VII) which allows for a wide variation in substituents as is necessary for achieving optimum phase behavior. A further advantageous aspect of the process according to the invention is the synthesis of (VIII) and its use as the common starting material for compounds of the formula (I) in which $R^1$ contains an alkylthio or an alkyloxy partial structure: besides a wide variation in $R_1$, $R_2$, can, in addition, be freely selected.

Using the process according to the invention subsequently explained in more detail, the compounds of the formula (I) can be prepared in which variations in $R^1$ and $R^2$, as are required for achieving optimum liquid-crystal properties, for example width and location of the $S_c$ phase, are possible in a particularly advantageous manner.

The process comprises reacting a 1-dimethylamino-3-dimethyliminio-2-(4-hydroxyphenyl)-1-propene perchlorate (VII) (prepared according to standard procedures known in the literature) with suitable reaction partners. Thus, (VII) is reacted with an S-alkylisothiourea bromide (XI) to give (VIII). $R^3$ has the meaning of $R_1$, $R_2$, and k=2, and the —$CH_2$— group adjacent to S in the general formulae VIII, IX and XI not be replaced by —O— or —S—.

By etherifying the OH group according to procedures known in the literature with a compound containing the radical $R^2$ in a suitable form, (VIII) gives the compounds (I) in which $R^1$ has an alkylthio partial structure.

By conversion of (VIII) to the sulfone (IX) which can be carried out according to methods known in the literature by means of oxidizing agents and further reaction thereof with compounds containing the radical $R^1$ in a suitable form, the compounds (X) can be obtained by nucleophilic substitution of the —$SO_2$—$R^3$ partial structure; preferably, an alkali metal alcoholate is used as the $R^1$-containing compound.

In analogy to the conversion of (VIII) to (I), the compounds (I) in which $R^1$ has an alkyloxy partial structure can subsequently also be obtained from (X) using an $R^2$ fragment.

By reaction of (VII) with the amidinium salts (II) to give compounds (X) and reaction of the latter by etherification of the free OH group with a compound containing the radical $R^2$ in a suitable form, the compounds (I) in which $R^1$ has an alkyl partial structure can be obtained.

The following examples are intended to illustrate the invention in more detail:

EXAMPLES 1–32

2-(Hexylthio)-5-(4-hydroxyphenyl)-pyrimidine (VII3) $R^3=C_6H_{13}$)

A solution of 812 g (2.55 mol) of (VII) and 1,339 g (5.55 mol) of (XI, $R^3=C_6H_{13}$) in 2 liters of pyridine is stirred at 80° C. for 6 hours. After standing at 25° C. for 12 hours, the mixture is poured onto ice/sulfuric acid; the resulting mixture having a pH of 3 is extracted with dichloromethane, and the extract is chromatographed over $SiO_2$ using dichloromethane/methanol 99:1. The product which is obtained as an oil is crystallized from n-hexane to give 458 g (62% of theory) of crystals of melting point 70°–72° C.

(S)-2-Heptylthio-5-[4-(6-methyloctyloxy)phenyl]-pyrimidine 0.45 g (0.015 mol) of sodium hydride (80% strength) is added to a solution of 3.0 g (0.01 mol) of (VIII, $R^3=C_7H_{15}$) in 20 ml of dimethylformamide and, after the evolution of gas stops, 3.1 g (0.015 mol) of (S)-6-methyloctyl bromide are added to the mixture. After 8 hours, the mixture is poured into 200 ml of $H_2O$ extracted with dichloromethane, and the extract is chromatographed over $SiO_2$ using dichloromethane/methanol 97:3. Recrystallization from n-hexane gives 2 g (46% of theory) of colorless crystals: $[\alpha]_D^{25}$: +3.76 (c=5, $CH_2Cl_2$); K 44.6 $S_c^*$ 52.5 $S_A$ 59.8 I.

The following examples are obtained analogously (S)-2-hexylthio-5-[4-(6-methyloctyloxy)phenyl]-pyrimidine. $[\alpha]_D^{25}$: +3.8 (c=5, $CH_2Cl_2$). K 46.8 $S_c^*$ 51.3 $S_A$ 62.5 I.

(S)-2-octylthio-5-[4-(6-methyloctyloxy)phenyl]-pyrimidine. $[\alpha]_D^{25}$: +3.52 (c=5; $CH_2Cl_2$). K 28.3 $S_c^*$ 55.4 $S_A$ 60 I.

(R,S)-2-octylthio-5-[4-(methylhexyloxy)phenyl]-pyrimidine. K 24 $S_c$ 36 $S_A$ 49.8 I.

(S) -2-nonylthio-5-[4-(6-methyloctyloxy)phenyl]-pyrimidine. $[\alpha]_D^{25}$: +3.4 (c=5, $CH_2Cl_2$). K 28.1 $S_c^*$ 53.5 $S_A$ 60.5 I.

(S)-2-decylthio-5-[4-(6-methyloctyloxy)phenyl]-pyrimidine. $[\alpha]_D^{25}$: +1.8 (c=5, $CH_2Cl_2$). K 35.7 $S_c^*$ 54.6 $S_A$ 59.9 I.

(S)-2-undecylthio-5-[4-(6-methyloctyloxy)phenyl]-pyrimidine. $[\alpha]_D^{25}$: +3.6 (c=5, $CH_2Cl_2$). K 30.8 $S_c^*$ 50.5 $S_A$ 56.7 I.

(S)-2-dodecylthio-5-[4-(6-methyloctyloxy)phenyl]-pyrimidine. $[\alpha]_D^{25}$: +3.16 (c=5, $CH_2Cl_2$). K 39.5 $S_c^*$ 52 $S_A$ 57 I.

(S)-2-octylthio-5-[4-(7-methylnonyloxy)phenyl]-pyrimidine. $[\alpha]_D^{25}$ +3.16 (c=5, $CH_2Cl_2$). K 45.2 $S_c^*$ 55.2 $S_A$ 59.4 I.

(S)-2-octylthio-5-[4-(8-methyldecyloxy)phenyl]-pyrimidine. $[\alpha]_D^{25}$: +3.08 (c=5, $CH_2Cl_2$). K 55.4 $S_c^*$ 63 $S_A$ 65.3 I.

(S)-2-(6-methyloctylthio)-5-(4-octyloxyphenyl)-pyrimidine. $[\alpha]_D^{25}$: +4.2 (c=5, $CH_2Cl_2$). K [15 $S_3$ 24.5 $S_c^*$ 55.6 $S_A$] 55.8 $S_A$ 64.3 I.

(S),(S)-2-(6-methyloctylthio)-5-[4-(6-methyloctyloxy)-phenyl]pyrimidine. $[\alpha]_D^{25}$: +9.0 (c=3, $CH_2Cl_2$). K [26 $S_c^*$ 43.8 $S_A$ 48]52.9 I.

2-heptylthio-5-(4-heptyloxyphenyl)pyrimidine. K 40.4 $S_c$ 42 $S_A$ 72.1 I.

2-heptylthio-5-(4-octyloxyphenyl)pyrimidine. K [10.8 $S_G$ 35.5] 39.4 $S_c$ 50.7 $S_A$ 74.6 I.

2-octylthio-5-(4-octyloxyphenyl)pyrimidine. K [18 $S_G$ 40] 51 $S_c$ 55 $S_A$ 74.8 I.

2-octylthio-5-(4-nonyloxyphenyl)pyrimidine. K [23.2 $S_G$ 38.1]52 $S_c$ 58 $S_A$ 75.8 I.

2-nonylthio-5-(4-octyloxyphenyl)pyrimidine. K [31.6 $S_G$ 40.5] 47.6 $S_c$ 54.5 $S_A$ 74.1 I.

2-nonylthio-5-(4-nonyloxyphenyl)pyrimidine. K [19.5 $S_G$ 38.5] 4.5 $S_c$ 57 $S_A$ 74.8 I.

2-nonylthio-5-(4-decyloxyphenyl)pyrimidine. K [27 $S_G$ 54] 58.8 $S_c$ 69.3 $S_A$ 75.7 I.

2-decylthio-5-(4-heptyloxyphenyl)pyrimidine. K[32 $S_C$ 45] 52.3 $S_A$ 70.5 I.

2-decylthio-5-(4-octyloxyphenyl)pyrimidine. K [24.5 $S_G$ 42.2 $S_c$] 54.8 $S_c$ 59.7 $S_A$ 74 I.

2-decylthio-5-(4-nonyloxyphenyl)pyrimidine. K [26.9 $S_G$ 42.2 $S_c$] 54.7 $S_c$ 59.7 $S_A$ 73.9 I.

2-decylthio-5-(4-decyloxyphenyl)pyrimidine. K [35.3 $S_G$ 57.8 $S_c$] 62.1 $S_c$ 71 $S_A$ 75 I.

2-decylthio-5-(4-undecyloxyphenyl)pyrimidine. K [42.5 $S_G$ 61.8 $S_c$] 64.5 $S_c$ 73.9 $S_A$ 75 I.

2-decylthio-5-(4-dodecyloxyphenyl)pyrimidine. K [48 $S_G$ 67.2] 69.2 $S_c$ 75.6 I.

2-undecylthio-5-(4-octyloxyphenyl)pyrimidine. K [46.8 $S_c$ 53.4] 61.4 $S_A$ 74.5 I.

2-undecylthio-5-(4-nonyloxyphenyl)pyrimidine. K [50.0 $S_c$ 54.7] 60.0 $S_A$ 73.4 I. K [45.7 $S_c$ 58.6] 62 $S_c$ 70.9 $S_A$ 74.8 I.

2-undecylthio-5-(4-undecyloxyphenyl)pyrimidine. K [56.3 $S_c$ 63.0] 65 $S_c$ 74.2 $S_A$ 74.7 I.

2-undecylthio-5-(4-dodecyloxyphenyl)pyrimidine. K [45 $S_G$ 68] 71 $S_c$ 75 I.

2-dodecylthio-5-(4-dodecyloxyphenyl)pyrimidine. K 64.2 $S_G$ 70.5 $S_c$ 75.2 I.

EXAMPLES 33–40

2-(Hexylsulfonyl)-5-(4-hydroxyphenyl)pyrimidine. (IX, $R^3=C_6H_{13}$).

952 ml of hydrogen peroxide (35% strength) are slowly added at 20° C. to a solution of 512 g (1.78 mol) of (VIII, $R^3=C_6H_{13}$) in 2.4 liters of acetic acid. The mixture is subsequently heated at 50° C. for 5 hours. After standing for 12 hours at 25° C., the solid is separated off and dried to give 310 g (54% of theory) of colorless crystals of melting point 134°-137° C.

2-(Nonyloxy)-5-(4-hydroxyphenyl)pyrimidine. (X, $R^1 = C_9H_{19}$).

36.7 g (0.76 mol) of sodium hydride (50% strength) are added to a solution of 133 g (0.92 mol) of 1-nonanol in 1.2 liters of dimethylformamide. After 1 hour, 98 g (0.31 mol) of (IX, $R^3=C_6H_{13}$) are carefully added in portions; a vigorous evolution of gas is accompanied by an increase in temperature to 54° C. After standing for 12 hours, the mixture is poured into 8 liters of $H_2O$, the solid is separated off, dried and washed with hexane to give 49 g (51% of theory) of crystals of melting point 89°-90° C.

2-Octyloxy-5-(4-octyloxyphenyl) pyrimidine. 0.45 g (0.015 mol) of sodium hydride (80% strength) are added to a solution of 3 g (0.01 mol) of (X, $R^1 = H_{17}C_8O$) in 50 ml of dimethylformamide. After evolution of $H_2$ has stopped, 3.6 g (0.015 mol) of octyl iodide are added. 7 hours later, the mixture is poured into 500 ml of $H_2O$, extracted with dichloromethane, and the extract is chromatographed over $SiO_2$ using dichloromethane. Recrystallization from n-hexane gives 2.2 g (54% of theory) of colorless crystals; K [54.7 $S_c$ 70.9] 75.8 $S_A$ 99.8 I.

The following examples are obtained analogously:

(S)-2-nonyloxy-5-[4-(6-methyloctyloxy)phenyl]-pyrimidine. $[\alpha]_D^{25}$: +3.4 (c=5, $CH_2CL_2$). K 77.7 $S_c^*$ 79.2 $S_A$ 84.7 I.

2octyloxy-5-(4-nonyloxyphdnyl)pyrimidine. K [56.9 $S_c$ 71] 75.8 $S_A$ 100 I.

(S),(S)-2-(7-methylnonyloxy)-5-[4-(6-methyloctyloxy)-phenyl]-pyrimidine. $[\alpha]_D^{25}$: +6.4 (c=5, $CH_2Cl_2$). K 70 [48 $S_c^*$ 66 $S_A$ 71] $S_A$ 71 I.

2-nonyloxy-5-[4-(7methyloctyloxy)phenyl]pryimidine. K 79 $S_c$ 83 $S_A$ 89 I.

(S)-2-octyloxy-5-[4-(6-methyloctyloxy)phenyl]-pyrimidine. $[\alpha]_D^{25}$: +4.06 (c=5, $CH_2Cl_2$). K 72.8 $S_c^*$ $S_A$ 86.3 I.

EXAMPLES 41-45

2-Nonyloxy-5-[4-(3,6-dioxadodecyloxy)phenyl]-pyrimidine. 2.2 g (0.007 mol) of (X,$R^1=H_{19}C_9O$) and 1.33 g (0.007 mol) of diethylene glycol monohexyl ether are added to a mixture of 1.8 g (0.007 mol) of triphenylphosphine and 1.1 ml (0.007 ml) of diethyl azodicarboxylate in 20 ml of tetrahydrofuran which had stopped reacting. After standing for 3 days, the mixture is evaporated to dryness in vacuo, the residue is taken up in dichloromethane and chromatographed over $SiO_2$ using dichloromethane: recrystallization from n-hexane gives 1.6 g (50% of theory) of colorless crystals. K [42 $S_A$ 44 I.] 48 I.

The following examples are obtained analogously:

2-nonyloxy-5-[4-(10-undecen-1-yl)oxyphenyl]-pyrimidine. K [62 $S_3$ 67 $S_c$ 81 $S_A$ 91] 83 $S_A$ 91 I.

(S)-2-(4-decyloxybenzyloxy)-5-[4-(6-methyloctyloxy)phenyl]pyrimidine. $[\alpha]_D^{25}$: +2.4 (c=5, $CH_2Cl_2$). K 122 $S_c^*$ 134 I.

2-octyloxy-5-[4-(4-decyloxyphenyl)methyloxyphenyl]-pyrimidine. K [116.7 $S_G$ 130.5 $S_c$] 133.4 $S_c$ 150.0 $S_A$ 157 I.

2-undecylthio-5-[4-(10-undecen-1-yl)oxyphenyl]-pyrimidine. K 56.0 $S_3$ 56.3 $S_c$ 66.3 $S_A$ 68.0 I.

EXAMPLES 46-49

2-Octyl-5-(4-hydroxyphenyl)pyrimidine. (X, $R^1 = C_8H_{17}$)

108 g (0.56 mol) of (II, $R^1 = C_8H_{17}$) and also 206 ml of sodium methylate solution (30% strength in methanol) are added to a suspension of 120 g (0.376 mol) of (VII) in 1 liter of methanol. After heating at 65° C. for 12 hours, the mixture is evaporated to dryness in vacuo, and the portion of the residue which is soluble in dichloromethane is chromatographed $SiO_2$ using dichloromethane. The oily fraction which contains the product crystallizes upon stirring it together with n-hexane to give 91 g (85% of theory) of crystals of melting point 94°-96° C.

(S)-2-Octyl-5-[4-(6-methyloctyloxy)phenyl]pyrimidine.

0.2 g (0.008 mol) of sodium hydride (80% strength) is added to a solution of 1.4 g (0.005 mol) of (X, $R^1=C_8H_{17}$) in 10 ml of dimethylformamide and, after the evolution of gas has stopped, 1.25 g (0.006 mol) of (S)-6-methyloctyl bromide are added. After standing for 8 hours, the mixture is poured into 100 ml of $H_2O$ extracted with dichloromethane, and the extract is chromatographed over $SiO_2$ using dichloromethane. Recrystallization from methanol gives 1 g (34% of theory) of colorless crystals, $[\alpha]_D^{25}$: +3.73 (c=10, $CH_2Cl_2$). K 40.2 $S_G^*$ 43.4 $S_c^*$ 57.8 $S_A$ 72.3 I.

The following examples are obtained analogously:

(S)-2-(6-methyloctyl)-5-(4-octyloxyphenyl)pyrimidine. $[\alpha]_D^{25}$: +3.24 (c=5, $CH_2Cl_2$). K 35.8 $S_3$ 44.5 $S_c^*$ 54 $S_A$ 70.5 I.

(S)-2-(8-methyldecyl)-5-(4-octyloxyphenyl)pyrimidine. $[\alpha]_D^{25}$: +3.04 (c=5, $CH_2Cl_2$). K 50 $S_3$ 60.4 $S_c^*$ 62.5 $S_A$ 74.2 I.

Method of measurement

If a small amount of a chiral compound is added to a (non-chiral) solvent, the plane of the plane-polarized light is rotated by a (characteristic) angle $\alpha$; this angle is indicated as follows: $[\alpha]_D^T$ (c=x, LM), the symbols having the following meaning: x=concentration of the solution in g/l, LM=solvent, D=589 nm (NaD line), T=temperature of the solution. The angle of rotation is determined in a polarimeter after a path length of the light of 10 cm.

We claim:

1. A 5-phenylpyrimidine. derivative of the formula (I)

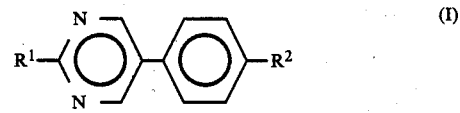

wherein $R_1$ is a straight-chain or branched alkyl group having from 8 to 16 carbon atoms, with or without an asymmetric carbon atom, and in $R^1$ a —$CH_2$— group adjacent to the pyrimidine nucleus can be replaced by —O— or —S—, and $R^2$ is a straight-chain or branched alkoxy group having from 7 to 15 carbon atoms, with or without an asymmetric carbon atom.

2. A 5-phenylpyrimidine derivative as claimed in claim 1, which is (S)-2-heptylthio-5-[4-(6-methyloctyloxy)phenyl]-pyrimidine, (S)-2-octylthio-5-[4-(6-methyloctyloxy)phenyl]-pyrimidine, (R,S)-2-octylthio-5-[4-(4-methylhexyloxy)phenyl]-pyrimidine, (S)-2-nonylthio-5-[4-(6-methyloctyloxy)phenyl]-pyrimidine,
(S)-2-decylthio-5-[4-(6-methyloctyloxy)phenyl]-pyrimidine,
(S)-2-undecylthio-5-[4-(6-methyloctyloxy)phenyl]-pyrimidine,
(S)-2-dodecylthio-5-[4-(6-methyloctyloxy)phenyl]-pyrimidine,
(S)-2-octylthio-5-[4-(7-methylnonyloxy)phenyl]-pyrimidine,
(S)-2-octylthio-5-[4-(8-methyldecyloxy)phenyl]-pyrimidine,
(S)-2-(6-methyloctylthio)-5-(4-octyloxyphenyl)-pyrimidine, (S),(S)-2-(6-methyloctylthio)-5-[4-(6-methyloctyloxy)phenyl]-pyrimidine,
2-heptylthio-5-(4-heptyloxyphenyl)pyrimidine,
2-heptylthio-5-(4-octyloxyphenyl)pyrimidine,
2-octylthio-5-(4-octyloxyphenyl)pyrimidine,
2-octylthio-5-(4-nonyloxyphenyl)pyrimidine,
2-nonylthio-5-(4-octyloxyphenyl)pyrimidine,
2-nonylthio-5-(4-nonyloxyphenyl)pyrimidine,
2-nonylthio-5-(4-decyloxyphenyl)pyrimidine,
2-decylthio-5-(4-heptyloxyphenyl)pyrimidine,
2-decylthio-5-(4-octyloxyphenyl)pyrimidine,
2-decylthio-5-(4-nonyloxyphenyl)pyrimidine,
2-decylthio-5-(4-decyloxyphenyl)pyrimidine,
2-decylthio-5-(4-undecyloxyphenyl)pyrimidine,
2-decylthio-5-(4-dodecyloxyphenyl)pyrimidine,
2-undecylthio-5-(4-octyloxyphenyl)pyrimidine,
2-undecylthio-5-(4-nonyloxyphenyl)pyrimidine,
2-undecylthio-5-(4-decyloxyphenyl)pyrimidine,
2-undecylthio-5-(4-undecyloxyphenyl)pyrimidine,
2-undecylthio-5-(4-dodecyloxyphenyl)pyrimidine,
2-dodecylthio-5-(4-dodecyloxyphenyl)pyrimidine,
2-octyloxy-5-(4-octyloxyphenyl)pyrimidine,
(S)-2-octyl-5-[4-(6-methyloctyloxy)phenyl]pyrimidine,
(S)-2-(6-methyloctyl)-5-(4-octyloxyphenyl)pyrimidine, or
(S)-b 2-(8-methyldecyl)-5-(4-octyloxyphenyl)pyrimidine.

* * * * *